United States Patent [19]

Seydel et al.

[11] Patent Number: 4,992,430
[45] Date of Patent: Feb. 12, 1991

[54] ANTI-BACTERIAL COMPOSITIONS COMPRISING A SUBSTITUTED BIS-(4-AMINOPHENYL)-SULFONE AND A DIHYDRO-FOLIC ACID REDUCTASE

[75] Inventors: Joachim K. Seydel, Borstel; Helmut Pieper; Gerd Kruger, both of Biberach; Klaus Noll, Warthausen; Johannes Keck, Biberach; Uwe Lechner, Ummendorf, all of Fed. Rep. of Germany

[73] Assignee: Dr. Karl Thomae GmbH, Biberach an Der Riss, Fed. Rep. of Germany

[21] Appl. No.: 302,158

[22] Filed: Jan. 26, 1989

Related U.S. Application Data

[60] Division of Ser. No. 62,291, Jun. 15, 1987, Pat. No. 4,829,058, which is a continuation of Ser. No. 732,024, May 8, 1985, Pat. No.

[30] Foreign Application Priority Data

May 22, 1984 [DE] Fed. Rep. of Germany ....... 3419009

[51] Int. Cl.⁵ .......................................... A61K 31/135
[52] U.S. Cl. .................................................... 514/155
[58] Field of Search ................. 514/155, 275; 544/375

[56] References Cited

U.S. PATENT DOCUMENTS

| | | | |
|---|---|---|---|
| 2,382,924 | 12/1940 | Tschesche | 564/154 |
| 2,454,835 | 11/1948 | Rawlins | 564/404 |
| 3,325,521 | 6/1967 | Elsilager et al. | 564/220 |
| 3,696,131 | 10/1972 | Matzner et al. | 564/154 |
| 3,903,275 | 9/1975 | Streiff | 514/275 |

FOREIGN PATENT DOCUMENTS 875562 8/1961 United Kingdom .
1164829 9/1969 United Kingdom .

OTHER PUBLICATIONS

Merk Index, 9th Edition, pp. 7853-54.
CA78:154899x Harwin et al.
CA104:81417g Lee et al.
CA106:90040x Korolkow et al.
CA100:215522r.
Kumar et al. CA89:123198r.
Popoff et al., J. Med. Chem. 1971, vol. 14, pp. 1166-1169.
Stacy et al., J.O.C. vol. 24, pp. 1892-6, 1959.

Primary Examiner—Jane T. Fan
Attorney, Agent, or Firm—D. E. Frankhouser; M. M. Timbers; A. R. Stempel

[57] ABSTRACT

Disclosed are substituted bis(4-aminophenyl)-sulfones of general formula

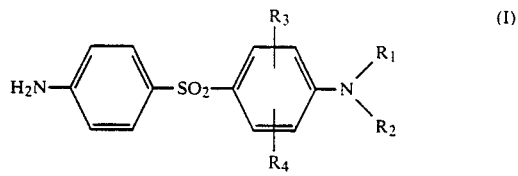

wherein
$R_1$ is hydrogen, alkyl or cycloalkyl; group,
$R_2$ is hydrogen or $C_1-C_3$ alkyl,
$R_3$ is nitrile, $C_1-C_3$ alkylaminocarbonyl, di $C_1-C_3$ alkylaminocarbonyl, $C_3-C_7$ N-cycloalkyl-$C_1-C_3$ alkylaminocarbonyl $C_1-C_3$ alkylamino, $C_1-C_3$, di alkylaminocarbonyl alkoxy, alkylaminosulfonyl, di $C_1-C_3$ alkylaminono, di$C_1-C_3$ alkylaminosulfonyl, hydroxy $C_1-C_3$ alkyl, $C_1-C_3$ alkylcarbonyl, amino $C_1-C_3$ alkyl or $C_1-C_3$ alkoxy $C_1-C_3$ alkyl group
or, when $R_1$ and $R_2$ are each hydrogen, $R_3$ can be hydroxy, hydroxycarbonyl $C_1-C_3$ alkoxy or di $C_1-C_3$ aminocarbonylalkoxy;
or, when $R_1$ is $C_1-C_3$ alkyl or $C_1-C_3$ cycloalkyl and $R_2$ is hydrogen or $C_1-C_3$ alkyl, $R_3$ can also be halogen, trifluoromethyl, nitro, amino, aminosulfonyl, aminocarbonyl, $C_1-C_3$ alkyl, carboxy or $C_1-C_3$ alkoxycarbonyl; and
$R_4$ is hydrogen or, when $R_1$ and $R_2$ are each hydrogen and $R_3$ is halogen or hydroxy, $R_4$ can also be halogen, hydroxy or $C_1-C_3$ alkoxy; or a nontoxic, pharmaceutically acceptable salt thereof. Also disclosed are pharmaceutical compositions comprising such compounds alone and in combination with dihydrofolic acid-reductase inhibitors. The compounds and compositions are useful for their inhibiting effect on bacteria, mycobacteria and plasmodia.

2 Claims, No Drawings

ANTI-BACTERIAL COMPOSITIONS COMPRISING A SUBSTITUTED BIS-(4-AMINOPHENYL)-SULFONE AND A DIHYDRO-FOLIC ACID REDUCTASE

This is a division of application Ser. No. 062,291 filed Jun. 15, 1987 now U.S. Pat. No. 4,829,058 issued May 9, 1989 which is a continuation of application Ser. No. 06/732,024 filed May 8, 1985 now abandoned.

BACKGROUND OF THE INVENTION

1. Field of the Invention

The present invention relates to the field of compounds useful for inhibiting bacteria, mycobacteria and plasmodia, particularly to sulfone compounds which are useful in this regard and in treating animals and humans suffering from infections of such organisms.

2. Brief Information Disclosure Statement

U.S. Pat. No. 2,385,899 describes the compound bis-(4-aminophenyl)-sulfone which has an inhibiting effect on the growth of bacteria, mycobacteria and plasmodia.

SUMMARY OF THE INVENTION

The present invention provides substituted bis-(4-aminophenyl)-sulfones of formula I

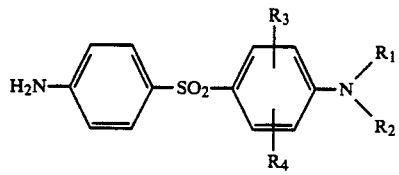

wherein $R_1$ is hydrogen, $C_1$-$C_7$ alkyl or $C_3$-$C_7$ cycloalkyl;

$R_2$ is hydrogen or $C_1$-$C_3$ alkyl;

$R_3$ is nitrile, $C_1$-$C_3$ alkylaminocarbonyl, di $C_1$-$C_3$ alkylaminocarbonyl, $C_3$-$C_7$ N-cycloalkyl $C_1$-$C_3$ alkylaminocarbonyl, $C_1$-$C_3$ alkylamino, di $C_1$-$C_3$ alkylamino, di $C_1$-$C_3$ alkylaminocarbonyl, $C_1$-$C_3$ alkoxy, $C_1$-$C_3$ alkylaminosulfonyl, di $C_1$-$C_3$ alkylaminosulfonyl, hydroxy $C_1$-$C_3$ alkyl, $C_1$-$C_3$ alkylcarbonyl, amino $C_1$-$C_3$ alkyl or $C_1$-$C_3$ alkoxy $C_1$-$C_3$ alkyl or, when $R_1$ and $R_2$ are each hydrogen, $R_3$ can be hydroxy or hydroxycarbonyl $C_1$-$C_3$ alkoxy or, when $R_1$ is $C_1$-$C_3$ alkyl or $C_3$-$C_7$ cycloalkyl and $R_2$ is hydrogen or $C_1$-$C_3$ alkyl, $R_3$ can also be halogen, trifluoromethyl, nitro, amino, aminosulfonyl, aminocarbonyl, $C_1$-$C_3$ alkyl, carboxy or $C_1$-$C_3$ alkoxycarbonyl; and $R_4$ is hydrogen, or when $R_1$ and $R_2$ are each hydrogen and $R_3$ is halogen or hydroxy in the 2-position, $R_4$ can also be halogen, hydroxy or $C_1$-$C_3$ alkoxy, or a nontoxic, pharmaceutically acceptable salt thereof.

One subgeneric aspect includes compounds of formula I wherein:

$R_1$ is hydrogen, $C_1$-$C_7$ alkyl or a $C_4$-$C_7$ cycloalkyl;

$R_2$ is hydrogen or methyl;

$R_3$ is nitrile, methylaminocarbonyl, N-cyclohexylmethylaminocarbonyl, methylamino, dimethylamino, dimethylaminocarbonylmethoxy, hydroxymethyl, hydroxyethyl, methylcarbonyl, aminocarbonyl or methoxymethyl;

or when, $R_1$ and $R_2$ are each hydrogen, $R_3$ can also be hydroxy or hydroxycarbonylmethoxy or, when $R_1$ is alkyl or cycloalkyl and $R_2$ is hydrogen or methyl, $R_3$ can also be chlorine, bromine, methyl, trifluoromethyl, nitro, amino or aminocarbonyl; and $R_4$ is hydrogen or, when $R_1$ and $R_2$ are each hydrogen and $R_3$ is hydroxy, chlorine or bromine in the 2-position, $R_4$ can also be chlorine, bromine, hydroxy or methoxy, or a nontoxic, pharmaceutically acceptable salts thereof.

A further subgeneric aspect includes compounds of formula I wherein:

$R_1$ is hydrogen, $C_1$-$C_3$ alkyl or $C_4$-$C_7$ cycloalkyl;

$R_2$ is hydrogen or, when $R_1$ is methyl, $R_2$ can also be methyl;

$R_3$ is chlorine, bromine, methyl, trifluoromethyl, hydroxymethyl, hydroxyethyl, methylamino, dimethylamino, cyano or methylcarbonyl in the 2-position; and $R_4$ is hydrogen; or a nontoxic, pharmaceutically acceptable addition salt thereof.

The present invention thus relates to the compounds of formula I above, the addition salts thereof, particularly the acid addition salts thereof with pharmaceutically acceptable inorganic or organic acids, pharmaceutical compositions containing these compounds including their addition salts, their preparation and the use thereof for inhibiting bacteria, mycobacteria and plasmodia and for treating animals and humans suffering from infections of such organisms.

This invention further relates to combinations of the substituted bis(4-aminophenyl)-sulfones of formula I including their nontoxic, pharmaceutically acceptable addition salts with a dihydrofolic acid-reductase inhibitor such as pyrimethamine, trimethoprim or trimethoprim derivatives.

DETAILED DESCRIPTION OF THE INVENTION

Examples of groups $R_1$ to $R_4$ include the following.

$R_1$ can be hydrogen, methyl, ethyl, n-propyl, isopropyl, n-butyl, isobutyl, n-pentyl, isoamyl, n-hexyl, n-heptyl, cyclobutyl, cyclopentyl, cyclohexyl or cycloheptyl.

$R_2$ can be hydrogen, methyl, ethyl, n-propyl or isopropyl.

$R_3$ can be cyano, methylaminocarbonyl, ethylaminocarbonyl, isopropylaminocarbonyl, dimethylaminocarbonyl, diethylaminocarbonyl, di-n-propylaminocarbonyl, N-methylethylaminocarbonyl, N-methyl-cyclopentylaminocarbonyl, N-methylcyclohexylaminocarbonyl, N-methylcycloheptylaminocarbonyl, N-ethyl-cyclohexylaminocarbonyl, methylamino, ethylamino, n-propylamino, isopropylamino, dimethylamino, diethylamino, diisopropylamino, N-methyl-ethylamino, N-ethyl-n-propylamino, dimethylaminocarbonylmethoxy, diethylaminocarbonylmethoxy, 2-dimethylaminocarbonylethoxy, 2-diethylaminocarbonylethoxy, methylaminosulfonyl, ethylaminosulfonyl, isopropylaminosulfonyl, dimethylaminosulfonyl, diethylaminosulfonyl, hydroxymethyl, 1-hydroxyethyl, 2-hydroxyethyl, 1-hydroxypropyl, 3-hydroxypropyl, methylcarbonyl, ethylcarbonyl, n-propylcarbonyl, aminomethyl, 2-aminoethyl, 3-aminopropyl, methoxymethyl, 2-methoxyethyl, ethoxymethyl, 2-ethoxyethyl, n-propoxymethyl, 2-n-propoxyethyl, hydroxy, hydroxycarbonylmethoxy, 2-hydroxycarbonylethoxy, 3-hydroxycarbonylpropoxy, 2-dimethylaminoethoxy, 2-diethylaminoethoxy, trifluoromethyl, nitro, amino, aminosulfonyl, aminocarbonyl, methyl, ethyl, n-propyl, isopropyl, carboxy, methoxycarbonyl, ethoxycarbonyl, n-propoxycarbonyl, isopropoxycarbonyl, fluorine, chlorine, bromine or iodine.

$R_4$ can be hydrogen, fluorine, chlorine, bromine, iodine, hydroxy, methoxy, ethoxy or n-propoxy.

According to the invention the compounds of formula I can be obtained by the following processes.

Method A In one method, compounds of formula I are made by reduction of a compound of formula II

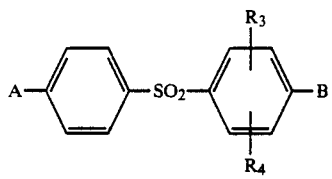

(II)

wherein $R_3$ and $R_4$ are as previously defined, one of A and B is nitro and the other is

wherein $R_1$ and $R_2$ are as previously defined, or is also nitro.

The reduction is conveniently carried out in a solvent or mixture of solvents such as water, methanol, ethanol, glacial acetic acid, ethyl acetate, dimethylformamide, water/ethanol or water/tetrahydrofuran in the presence of a reducing agent, e.g. with hydrogen in the presence of a hydrogenation catalyst such as Raney nickel, platinum or palladium/charcoal, with metals such as iron, tin or zinc in the presence of an acid such as hydrochloric or acetic acid, with salts such as iron(II)sulphate, tin(II)chloride/hydrochloric acid or sodium dithionite in the presence of a base such as sodium hydroxide solution or pyridine or with hydrazine in the presence of Raney nickel, at temperatures of 0° to 50° C., preferably at ambient temperature.

Method B In another method, one or two protecting groups are cleaved from a compound of formula III

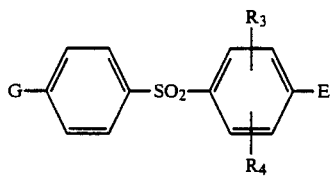

(III)

wherein $R_3$ and $R_4$ are as previously defined, E is amino, $C_1$-$C_7$alkylamino or $C_3$-$C_7$ cycloalkylamino protected by a protecting group, or is

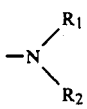

wherein $R_1$ and $R_2$ are as previously defined; and

G is an amino group optionally protected by a protecting group. At least one of E and G must be one of the above-mentioned groups protected by a protecting group.

Suitable protecting groups are the protecting groups conventionally used for amino groups, e.g. hydrolytically removable protecting groups such as acetyl, propionyl, benzoyl, p-toluenesulfonyl, methanesulfonyl or ethoxycarbonyl, or hydrogenolytically removable groups such as benzyl.

Any protecting group used is preferably split off by hydrolysis, e.g. with an acid such as hydrochloric, sulphuric or phosphoric acid or with a base such as sodium hydroxide or potassium hydroxide in a suitable solvent or mixture of solvents such as water, water/methanol, ethanol, water/ethanol, water/isopropanol or water/dioxan at temperatures of $-10°$ to 120° C., preferably ambient temperature to the boiling temperature of the reaction mixture, or by hydrogenolysis, e.g. with hydrogen in the presence of a hydrogenation catalyst such as palladium/charcoal in a suitable solvent such as methanol, ethanol, glacial acetic acid, ethyl acetate, dioxan or dimethylformamide at temperatures of 0° to 50° C., preferably at ambient temperature.

Method C Compounds of formula I wherein $R_3$ is cyano are prepared by dehydration of a compound of formula IV

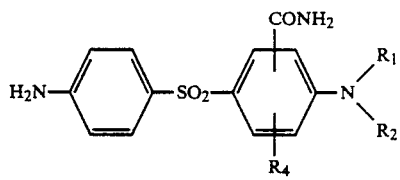

(IV)

wherein $R_1$, $R_2$ and $R_4$ are as previously defined.

The dehydration is conveniently carried out with a dehydrating agent such as phosphorus pentoxide, concentrated sulphuric acid, p-toluenesulphonic acid, thionylchloride, phosphorus oxychloride, sulfurylchloride, phosphoric acid or dicyclohexylcarbodiimide, optionally in a solvent such as methylene chloride, phyridine or chlorobenzene or in an excess of the dehydrating agent used such as thionyl chloride, phosphorus oxychloride, sulfurylchloride, or phosphoric acid at temperatures of 0° to 100°, preferably 20° to 80° C. However, the reaction can also be carried out without a solvent.

Method D Compounds of formula I wherein $R_3$ is hydroxycarbonylalkoxy or dialkylaminocarbonylalkoxy can be prepared by alkylation of a compound of formula V

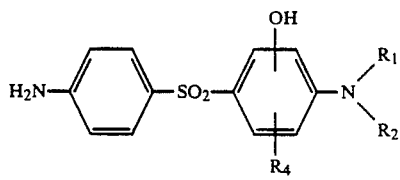

(V)

wherein $R_1$, $R_2$ and $R_4$ are as previously defined with a compound of formula VI $$X-Alk-CO-R_5$$ (VI)

wherein

Alk is a $C_1$-$C_3$ alkylene;

$R_5$ is hydroxy, $C_1$-$C_3$ alkoxy or di $C_1$-$C_3$alkylamino; and

X is a nucleophilically exchangeable group such as chlorine or bromine, optionally with subsequent hydrolysis.

The reaction is preferably carried out in a solvent such as diethylether, tetrahydrofuran, dioxan, methanol, ethanol, pyridine or dimethylformamide, optionally with a base such as sodium hydride, potassium hydride, potassium carbonate or potassium tert.butoxide at temperatures of 0° to 75° C., preferably at ambient temperature.

The optional subsequent hydrolysis is preferably carried out either with an acid such as hydrochloric, sulphuric, phosphoric or trichloroacetic acid or with a base such as sodium hydroxide or potassium hydroxide in a suitable solvent such as water, water/methanol, ethanol, water/ethanol, water/isopropanol or water/dioxan at temperatures of $-10°$ C. to 120° C., e.g. ambient temperature to the boiling temperature of the reaction mixture.

Method E Compounds of formula I wherein $R_3$ is aminocarbonyl, alkylamino-carbonyl, dialkylaminocarbonyl or dialkylaminocarbonylalkoxy can be prepared by reaction of a compound of formula VII

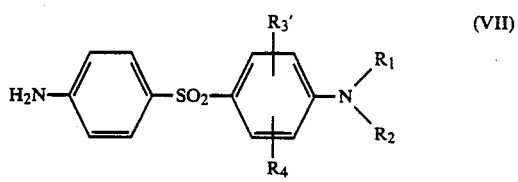

wherein $R_1$, $R_2$ and $R_4$ are as hereinbefore defined; and $R_3'$ is hydroxycarbonyl, hydroxycarbonyl-alkoxy or a reactive derivative thereof, with an amine of formula VIII

wherein $R_6$ is hydrogen atom or $C_1$-$C_3$ alkyl; and $R_7$ is hydrogen or $C_1$-$C_3$ alkyl, or reactive derivatives thereof.

The reaction is conveniently carried out in a solvent such as methylene chloride, chloroform, carbon tetrachloride, ether, tetrahydrofuran, dioxan, benzene, toluene, acetronitrile or dimethylformamide, optionally in the presence of an acid-activating agent or a dehydrating agent, e.g. in the presence of ethylchloroformate, thionylchloride, phosphorus trichloride, phosphorus pentoxide, N,N'-dicyclohexylcarbodiimide, N,N'-dicyclohexylcarbodiimide/N-hydroxy succinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine, which can simultaneously serve as solvent, at temperatures of $-25°$ C. to 250° C., preferably $-10°$ C. to the boiling temperature of the solvent used. The reaction can also be carried out without a solvent and furthermore any water formed during the reaction can be removed by azeotropic distillation, e.g. by heating with toluene using a water separator or by adding a drying agent such as magnesium sulphate or molecular sieve.

In this reaction it can also be advantageous to prepare an activated derivative of a compound of formula VII or VIII in the reaction mixture initially and then react this derivative with a compound of formula VIII or VII.

Method F Compounds of formula I wherein $R_3$ is hydroxymethyl, aminomethyl or 1-hydroxyalkyl can be prepared by reduction of a compound of formula IX

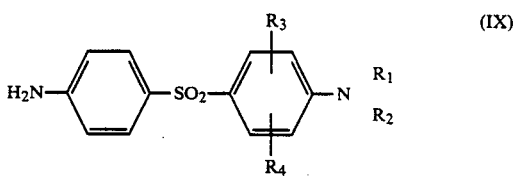

wherein $R_1$ and $R_2$ and $R_4$ are as previously defined; and $R_3''$ is hydroxycarbonyl, alkoxycarbonyl, aminocarbonyl or $C_2$-$C_4$ alkylcarbonyl.

The reaction is preferably carried out with a metal hydride such as sodium borohydride, lithium aluminium hydride or diborane in a solvent such as water, methanol, water/methanol, diethyl ether, tetrahydrofuran or dioxan at temperatures of 0° to 80° C., preferably ambient temperature to 70° C.

Method G Compounds of formula I wherein $R_1$ is alkyl or cycloalkyl and $R_2$ is hydrogen can be prepared by reduction of a compound of formula X

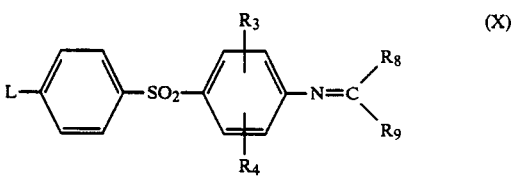

wherein $R_3$ and $R_4$ are as previously defined;

L is amino or nitro; and $R_8$ and $R_9$ together with the carbon atom between them are a $C_1$-$C_7$ alkylidene or a $C_3$-$C_7$ cycloalkylidene.

The reduction is preferably carried out in a suitable solvent such as methanol, ethanol, methanol/water, ethyl acetate, tetrahydrofuran or dioxan with nascent or catalytically activated hydrogen or with a hydride such as diborane, sodium borohydride or lithium aluminium hydride at temperatures of 0° to 50° C., preferably at ambient temperature.

If L is nitro, the reduction is particularly advantageously carried out in a solvent such as methanol or ethyl acetate with hydrogen in the presence of a hydrogenation catalyst such as platinum or palladium/charcoal and under a hydrogen pressure of 0 to 5 bar or with a complex metal hydride such as lithium aluminium hydride or diborane at temperatures of 0° to 50° C., preferably at ambient temperature.

If L in a compound of formula X is amino, the reduction is carried out particularly advantageously in a solvent such as methanol, methanol/water, tetrahydrofuran or dioxan with a complex metal hydride such as sodium borohydride or lithium aluminium hydride at temperatures of 0° to 50° C., preferably at ambient temperature.

If a compound of formula I is obtained wherein R₃ is alkoxycarbonyl or alkoxycarbonylalkoxy, it can be converted by hydrolysis into a corresponding compound of formula I wherein R₃ is hydroxycarbonyl or hydroxycarbonylalkoxy. If a compound of formula I is obtained wherein R₃ and/or R₄ is chlorine or bromine, it can be converted by hydrolysis or alcoholysis into a corresponding compound of formula I wherein R₃ is hydroxy or alkoxy in the 2 position and R₄ is chlorine or bromine.

This hydrolysis is conveniently carried out either with an acid such as hydrochloric or sulphuric acid or with a base such as sodium hydroxide or potassium hydroxide in a suitable solvent such as water, water/methanol, ethanol, water/ethanol, water/isopropanol or water/dioxan at temperatures of −10° C. to 120° C., e.g. at temperatures of ambient temperature to the boiling temperature of the reaction mixture.

The alcoholysis is conveniently carried out in a corresponding alcohol as the solvent such as methanol, ethanol or propanol, optionally in a pressure vessel, preferably with a base such as sodium hydroxide or potassium hydroxide at temperatures of 20° C. to 200° C., preferably 50° to 180° C.

The compounds of general formulae II to X used as starting materials are known from the literature or can be obtained by methods known from the literature.

Thus, for example, a compound of formula II or III can be obtained by reacting an alkali metal salt of a corresponding acylaminophenyl-sulfinic acid with a corresponding p-halonitrobenzene. A compound of formula XI

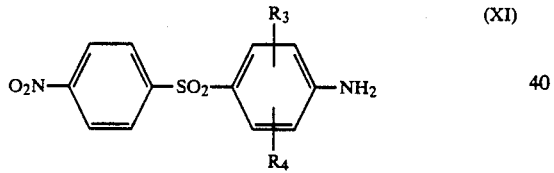

optionally obtained after splitting off an acyl protecting group, wherein R₃ and R₄ are as previously defined, can subsequently be converted by reductive amination into a compound of formula II or after tosylation, subsequent alkylation and reduction of the nitro group and optionally subsequent acylation into a compound of formula III.

Moreover, a compound of formula XII

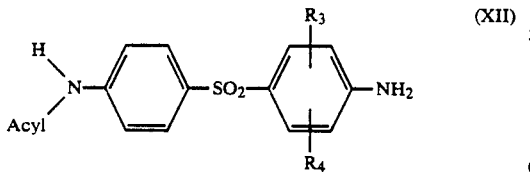

prepared by methods known from the literature, wherein R₃ and R₄ are as previously defined and Acyl is an organic acyl group, can be converted by reductive amination or by reduction of a Schiff's base obtained after reaction with a corresponding carbonyl compound into a compound of formula III wherein D is an aminoacyl group and E is

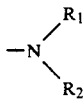

wherein, R₁ and R₂ are as previously defined.

Moreover a compound of formula XIII

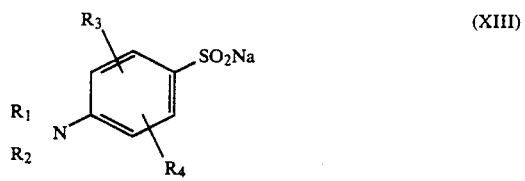

wherein

R₁ to R₄ are as previously defined and Na is a sodium ion, can be reacted with a 4-halonitrobenzene to form a corresponding diphenylsulfone of formula III.

A cycloalkylamino compound of formula II, however, is preferably obtained by reductive amination of a corresponding amino compound with a cycloalkanone in the presence of sodium cyanoborohydride or by reduction of the corresponding Schiff's base with a complex metal hydride.

A compound of formula X used as starting material is obtained by reacting a corresponding compound of formula XI with a corresponding carbonyl derivative, optionally in the presence of titanium(IV) chloride and optional subsequent reduction of the nitro group, for example with catalytically activated hydrogen.

As already mentioned hereinbefore, the new compounds of formula I including their nontoxic, pharmaceutically acceptable addition salts have an inhibiting effect on the growth of bacteria and parasites such as plasmodia and mycobacteria which is believed to be due to their inhibiting effect on 7,8-dihydropteroic acid-synthetase.

For example, the following compounds
A=4-Ethylamino-4'-amino-2-chloro-diphenylsulfone,
B=4'-Amino-2-chloro-4-isopropylamino-diphenylsulfone,
C=4-Ethylamino-4'-amino-2-methyl-diphenylsulfone,
D=4-Ethylamino-4'-amino-2-trifluoromethyl-diphenyl-sulfone,
E=4,4'-Diamino-2-hydroxymethyl-diphenylsulfone,
F=4,4'-Diamino-2-(1-hydroxyethyl)-diphenylsulfone,
G=4,4'-Diamino-2-(N,N-dimethylamino)-diphenylsulfone,
H=4,4'-Diamino-2-(N-methylamino)-diphenylsulfone,
I=4,4'-Diamino-2-cyano-diphenylsulfone,
K=4,4'-Diamino-2-methylcarbonyl-diphenylsulfone,
L=4'-Amino-2-methyl-4-methylamino-diphenylsulfone and
M=4'-Amino-2-methyl-4-propylamino-diphenylsulfone were tested for their biological activity in cell-free enzyme extract of *Plasmodiumberghei* as follows.

1. Preparation of the enzyme extract

Plasmodia are isolated from mouse blood infected with *Plasmodium berghei* in accordance with the following reference (Heidrich, H. -G. et al., Z. Parasitenkd. 59: 151 (1979). The plasmodia were opened by ultrasound. Proteins with 7,8-hydropteroic acid synthetase activity are concentrated by gel filtration.

2. Biological test system

The inhibiting effect on 7,8-dihydropteroic acid synthesis of plasmodia is determined as follows:

Under optimum reaction conditions, i.e. $V_{max}$ for the reaction which is to be inhibited, the concentration of inhibitor in the new compounds resulting in a 50% reduction in the enzyme synthesis performance is determined. For this purpose the quantity of 7,8-dihydropteroic acid synthesised from the enzyme extract is determined by means of high performance liquid chromatography (HPLC) using a UV detector after an incubation period of 4 hours. It was established that the synthesis of 7,8-dihydropteroic acid proceeded in a linear manner during this period.

The $i_{50}$ values obtained by this method for a selection of the compounds claimed and those of the comparison preparations bis (4-aminophenyl)sulfone (Dapsone ®, DDS) and $N^1$-(5,6-dimethoxy-4-pyrimidinyl)-sulfanilamide (Fanasil ®) are given in the following Table:

| Substance | $i_{50}$ [μM] |
| --- | --- |
| A | 2.10 |
| B | 2.67 |
| C | 2.62 |
| D | 5.86 |
| E | 4.90 |
| F | 10.40 |
| G | 12.90 |
| H | 4.10 |
| I | 12.48 |
| K | 12.90 |
| L | 2.94 |
| M | 2.44 |
| Dapsone ® | 12.41 |
| Fanasil ® | 200 |

Moreover, in contrast to Dapsone ®, the new compounds are well tolerated and in particular show a very low methemoglobin formulation. For example, when substances I and M are administered to cats in a dosage of 200 mg/kg by oral route no methemoglobin formulation is detected.

On the basis of their biological properties the new compounds and the nontoxic, pharmaceutically acceptable acid addition salts thereof are suitable for the treatment of bacterial diseases, malaria and leprosy.

In monotherapy the single dosage for adults is from 100 to 300 mg, preferably 100 to 200 mg, once or twice a day. In combined therapy with a dihydrofolic acid-reductase inhibitor the single dose for adults is 50 to 200 mg + 5 to 30 mg of pyrimethamine, preferably 50 to 150 mg + 6.25 to 25 mg of pyrimethamine.

The new compounds and the nontoxic, pharmaceutically acceptable acid addition salts thereof optionally combined with a dihydrofolic acid reductase inhibitor such as pyrimethamine, trimethoprim or a trimethoprim derivative, can be made into preparations such as plain or coated tablets, capsules or suspensions.

The following Examples illustrate the invention:

EXAMPLE 1

3-Cyano-4,4'-diamino-diphenylsulfone (a) 3-Cyano-4,4'-dinitro-diphenylsulfide (a) First, 4-nitrothiophenol (10 g, 0.064 mol) is dissolved by stirring in a solution of sodium hydroxide (2.8 g) in water (10 ml) and ethanol (100 ml). Then, 5-chloro-2-nitrobenzonitrile (11.8 g, 0.064 mol) is added in order to reflux the resulting solution for 1 hour with stirring, whereupon a yellow substance is precipitated. After the suspension has been cooled the product obtained is suction filtered, washed with ethanol and then dried. This crude product is recrystallised from methanol.

Yellow crystals, m.p.: 123°–126° C., (b) 3-Cyano-4,4'-dinitro-diphenylsulfone

Next, the 3-cyano-4,4'-dinitro-diphenylsulfide (10 g, 0.033 mol) is dissolved by heating in glacial acetic acid (150 ml). Perhydrol (20 ml) is added dropwise to this solution with stirring at ambient temperature. After it has all been added the mixture is refluxed for a further 1 ½ hours during which a white substance is precipitated. After the suspension has cooled the substance is suction filtered, washed with ethanol and water and then dried.

Yellow crystals, m.p.: 188°–190° C.

(c) 3-Cyano-4,4'-diamino-diphenylsulfone

The 3-cyano-4,4'-dinitro-diphenyl-sulfone (2 g, 0.006 mol) is added in batches, with stirring, at 10° to 20° C., to a mixture of $SnCl_2 \times 2H_2O$ (8.1 g) and conc. hydrochloric acid (15 ml). After it has all been added, the mixture is stirred for a further 4 hours at ambient temperature and then the mixture is stirred into 10N sodium hydroxide solution (50 ml) while being intensively cooled. The product precipitated is suction filtered and dried. The crude product is purified by column chromatography. For this, the substance is dissolved in ethyl acetate and chromatographed over silica gel (200 g, 0.063–0.2 mm), ethyl acetate and methylene chloride 1:1 being used as eluant. The corresponding fractions are combined and evaporated.

Colorless crystals, m.p.: 240°–242° C.

EXAMPLE 2

4,4'-Diamino-2,6-dibromo-diphenylsulfone (a) 3,4,5-Tribromonitrobenzene

At 20° C., with stirring and cooling with ice, a solution of 2,6-dibromo-4-nitro-aniline (47.2 g) in acetic acid (1.6 liters) is slowly poured into a solution of sodium nitrite (12 g) in concentrated sulphuric acid (85 ml). Then, the mixture is stirred for 20 minutes at ambient temperature. The solution thus prepared is then slowly added with stirring and cooling with ice to a solution of copper (I) bromide (12.8 g) in 63% hydrobromic acid (40 ml). After it has all been added the mixture is stirred for a further 30 minutes. It is diluted with water, the precipitate is filtered off and washed with water. This crude product is recrystallized from methanol.

Colorless crystals, m.p. 110° C.

(b) 4'-Acetamino-2,6-dibromo-4-nitro-diphenylsulfide

Sodium (2.9 g) is dissolved in absolute ethanol (520 ml). Then, 4-acetamino-thiophenol (22 g) is dissolved in the sodium alkoxide solution thus prepared, and 3,4,5-tribromonitrobenzene (44.5 g) is added. The mixture is then heated to reflux temperature for 5 hours. After cooling it is poured onto water, extracted exhaustively with ethyl acetate, the combined ethyl acetate extracts are washed with water, dried over sodium sulfate and evaporated down to a small volume. The material precipitated is suction filtered and recrystallized from methanol.

Colorless crystals, m.p.: 208°–209° C.

(c) 2,6-Dibromo-4,4'-dinitro-diphenylsulfone

Next, 4'-acetamido-2,6-dibromo-4-nitro-diphenylsulfide (5 g) is dissolved in glacial acetic acid (40 ml) by heating. Perhydrol (20 ml) is added dropwise to this solution at ambient temperature with stirring. After it has all been added the mixture is stirred at reflux temperature for a further 2 hours. On cooling, yellow crystals are precipitated which are suction filtered and washed first with water and then with methanol.

M.p.: 170°–175° C.

(d) 4,4'-Diamino-2,6-dibromo-diphenylsulfone

Tin (II) chloride dihydrate (17 g) is dissolved in concentrated hydrochloric acid (17 ml). Then, 2,6-dibromo-4,4'-dinitro-diphenylsulfone (3.96 g) is added to this solution with a spatula, with stirring, and the temperature rises to about 50° C. The mixture is stirred for a further 2 hours and left to stand for 16 hours at ambient temperature. Then it is slowly poured into 10N sodium hydroxide solution (40 ml) with stirring and cooling with ice. The precipitate is filtered off and washed thoroughly with water and then with isopropanol.

Colorless crystals, m.p.: 168°–170° C. (decomp.).

EXAMPLE 3

4,4'-Diamino-2-hydroxy-6-methoxy-diphenylsulfone

First, 4,4'-diamino-2,6-dibromo-diphenylsulfone (1 g) (Example 2) is added to potassium hydroxide (1.12 g) in water (0.15 ml) and methanol (25 ml). This mixture is heated to 150° C. under pressure for 14 hours. It is then diluted with water, the insoluble matter is filtered off and the filtrate is concentrated to dryness in vacuo. The solid residue is taken up in a little water. The aqueous solution is acidified with 2N hydrochloric acid up to pH 5 and the colorless precipitate obtained is suction filtered, washed with water and dried. M.p.: 127° C. (decomp.).

EXAMPLE 4

2-Bromo-4,4'-diamino-6-hydroxy-diphenylsulfone

Here, 4,4'-diamino-2,6-dibromo-diphenylsulfone (1 g) (Example 2) is added to a solution of potassium hydroxide (1.12 g) in water (0.15 ml) and tert.butanol (50 ml). This mixture is heated to 150° C. under pressure for 10 hours. It is then diluted with water, filtered to remove the insoluble matter and the filtrate is evaporated to dryness in vacuo. The solid residue is taken up in a little water. The aqueous solution is acidified with 2N hydrochloric acid up to pH 5 and the colorless precipitate obtained is suction filtered and washed with water and dried.

| IR spectrum (KBr): | 3000–3600 cm$^{-1}$ | OH assoc. |
| --- | --- | --- |
| | 3360, 3470 cm$^{-1}$ | NH$_2$ free |
| | 3210 cm$^{-1}$ | NH$_2$ assoc. |
| | 2840 cm$^{-1}$ | OCH$_3$ |
| | 1140, 1320 cm$^{-1}$ | SO$_2$ |

EXAMPLE 5

4-Ethylamino-4'-amino-2-methyl-diphenylsulfone (a) 4'-Acetamino-2-methyl-4-tosylamino-diphenylsulfide Here, 4'-acetamino-4-amino-2-methyl-diphenyl-sulfide (2.7 g) J. Org. Chem. 15, 400 (1950)) is dissolved in dry pyridine (7 ml). At ambient temperature, p-toluenesulfonic acid chloride (2.85 g) is added to this solution and the mixture is left to stand for 2 days at ambient temperature. Then it is heated to 90° C. for 6 hours to complete the reaction and after cooling, it is diluted with water (50 ml). The solids precipitated are suction filtered and carefully washed with water and then with petroleum ether and dried. M.p.: 130°–134° C.

(b) 4'-Acetamino-4-(N-ethyl-N-tosyl-amino)-2-methyldiphenylsulfide

The 4'-acetamino-2-methyl-4-tosylamino-diphenylsulfide (3.5 g), ethyl iodide (2 g) and dry potassium carbonate (1.5 g) are heated to 95° C. in dimethylformamide (50 ml) with stirring for 17 hours. After cooling the mixture is poured onto water. The solids precipitated are suction filtered and thoroughly washed with water and petroleum ether and then dried.

IR spectrum (methylene chloride):
3420 cm$^{-1}$ NH
1695 cm$^{-1}$ amide
1505 cm$^{-1}$ sulfonamide (c) 4'-Acetamino-4-(N-ethyl-tosylamino)-2-methyldiphenylsulfone The 4'-acetamino-4-(N-ethyl-tosylamino)-2-methyl-diphenylsulfide (2.25 g) is heated to 90° C. for 3 hours in acetic acid (20 ml) and perhydrol (6 ml). After cooling, the mixture is diluted with water, the solids precipitated are carefully washed with water and petroleum ether and dried. This crude product is chromatographed over silica gel with a methylene chloride/methanol mixture (25:1). Light yellow foamy substance.

| IR spectrum (KBr): | 3420 cm$^{-1}$ | NH |
| --- | --- | --- |
| | 1680 cm$^{-1}$ | amide |
| | 1500 cm$^{-1}$ | sulfonamide |
| | 1315, 1150 cm$^{-1}$ | sulfone |

(d) 4-Ethylamino-4'-amino-2-methyl-diphenylsulfone

The 4'-acetamino-4-(N-ethyl-tosylamino)-2-methyl-diphenylsulfone (1.05 g) is dissolved in concentrated sulfuric acid (6 ml). This solution is left to stand for 4 hours at ambient temperature, then mixed with ice and neutralized with ammonia. The solids precipitated are suction filtered. The crude product consisting of 4'-acetamino-4-ethylamino-2-methyl-diphenylsulfone is heated to boiling temperature for 1 hour in a mixture of concentrated hydrochloric acid/water=1/1. After cooling, it is poured onto water and neutralized with ammonia. The solids precipitated are washed with water and dried. M.p.: 166°–167° C.

EXAMPLE 6

4'-Amino-2-methyl-4-methylamino-diphenylsulfone

First, 4'-acetamino-2-methyl-4-(N-methyl-tosyl-amino)-diphenylsulfone (3.5 g); prepared analogously to Example 5, is heated to reflux temperature with phenol (3.5 g) in 48% hydrobromic acid (120 ml) for 1 ½ hours. After cooling, the mixture is poured onto ice, neutralized with sodium hydroxide, extracted with methylene chloride, dried over sodium sulfate and concentrated to dryness in vacuo. The solid residue is dissolved in absolute ethanol. This solution is acidified with ethanolic hydrochloric acid and then mixed with ether until crystallization starts. The crystals are suction filtered, washed with ethanol/ether and dried.

Dihydrochloride: colorless crystals, mp.: 232°–235° C.

M.p. of the base: 150°–153° C.

EXAMPLE 7

4'-Amino-2-methyl-4-n-propylamino-diphenylsulfone

The title compound is prepared from 4'-acetamino-2-methyl-4-(N-n-propyl-tosylamino)-diphenylsulfone with phenol and hydrobromic acid analogously to Example 6.

Colorless crystals, m.p.: 170°–173° C.

EXAMPLE 8

4-Ethylamino-4'-amino-2-chloro-diphenylsulfone (a) 4'-Acetamino-2-chloro-4-p-tosylamino-diphenylsulfone Here, p-tosyl chloride (190 mg) is dissolved in anhydrous pyridine (5 ml) and 4'-acetamino-4-amino-2-chlorodiphenylsulfone (300 mg) (synthesised according to J. Med. Chem. 14:1166 (1971)) is added. The mixture is kept at ambient temperature for 3 hours with stirring and for 1 hour at 50° C. After cooling, it is poured onto ice/HCl and the precipitate is suction filtered.

Recrystallization from MeOH/H₂O, colorless crystals.

(b) 4-Ethylamino-4'-amino-2-chloro-diphenylsulfone

Then, 4'-acetamino-2-chloro-4-p-tosylaminodiphenylsulfone (70 mg) and potassium carbonate (25 mg) are suspended in dimethylformamide (5 ml). After the addition of ethyl iodide (200 μl) the mixture is heated to 90° C. (bath) for 24 hours. After cooling, the mixture is poured onto ice and the precipitate is removed by suction filtering. The dry residue is dissolved in conc. $H_2SO_4$ (0.5 ml) with stirring. After 1 hour, it is poured onto ice and the pH is adjusted to 4 to 6 with ammonia. The precipitate is suction filtered, mixed with 20% hydrochloric acid (10 ml) and refluxed for 1 hour. After cooling, the mixture is neutralized with ammonia and the precipitate is suction filtered.

Recrystallization from MeOH/H₂O.

M.p.: 173°–175° C.

EXAMPLE 9

4'-Amino-2-chloro-4-isopropylamino-diphenylsulfone

Here, 4'-amino-2-chloro-4-p-tosylamino diphenylsulfone (300 mg), potassium carbonate (100 mg), isopropylbromide (500 μl) and dimethylformamide (10 ml) are heated to 90° C. (bath) for 72 hours. After cooling, the mixture is poured onto ice and the precipitate is suction filtered. The dry residue is dissolved in conc. $H_2SO_4$ (0.5 ml) with stirring. After 1 hour it is poured onto ice and the pH is adjusted to 4 to 6 with $NH_3$. The precipitate obtained is suction filtered, mixed with 20% hydrochloric acid (10 ml) and refluxed for 1 hour. After cooling, it is neutralized with ammonia and the precipitate is suction filtered.

Recrystallization from methanol. Colorless solids.

| NMR (DMSO) 90 MHZ | 1.08–1.15 | 6H | Doublet CH(CH₃)₂ |
|---|---|---|---|
| | 3.40–3.70 | 1H | Multiplet CH (CH₃)₂ |
| | 6.04 | 2H | Singlet NH₂ |
| | 6.50–6.70 | 5H | Multiplet NH, aromatic H |
| | 7.40–7.50 | 2H | Doublet, aromatic H |
| | 7.75–7.85 | 1H | Doublet, aromatic H |

EXAMPLE 10

2-Carboxymethyloxy-4,4'-diamino-diphenylsulfone (a) 2-Ethoxycarbonylmethyloxy-4,4'-diamino-diphenylsulfone First, 4,4'-diamino-2-hydroxydiphenylsulfone (7.9 g, 0.03 mol) (J. Scientific and Industrial Research 17B, 192 (1958)) is dissolved in tetrahydrofuran (160 ml). This solution is mixed with sodium hydride (1.3 g, 0.03 mol) under a nitrogen atmosphere with stirring at ambient temperature. The mixture begins to foam and toward the end of the addition a thick crystal slurry is precipitated. By adding dimethylformamide (250 ml) a clear solution is obtained. Ethyl bromoacetate (3.3 ml. 0.03 mol) is added dropwise, the mixture is stirred for 3.5 hours at ambient temperature and then evaporated to dryness in vacuo. The residue is stirred with a mixture of water and methylene chloride, whereupon a solid crystalline material is obtained which is suction filtered from the solvent mixture, stirred with methylene chloride/water once more, suction filtered again and dried. The product thus obtained has a melting point of 178° to 183° C.

(b) 2-Carboxymethyloxy-4,4'-diamino-diphenylsulfone

The 2-ethoxycarbonylmethyloxy-4,4'-diaminodiphenylsulfone (2.8 g 0.008 mol) is heated to boiling for half an hour in a mixture of ethanol (280 ml), sodium hydroxide (2.8 g, 0.007 mol) and water (56 ml). The mixture is left to cool, acidified with conc. hydrochloric acid to a pH of 1 and evaporated to dryness in vacuo. Then, the residue is briefly boiled with alcohol, filtered to remove any insoluble matter, the filtrate is evaporated to dryness in vacuo and the residue is purified by chromatography on silica gel, eluant methylene chloride/methanol (1:1). The product thus obtained is recrystallized from ethanol and has a melting point of 255°–260° C. (decomp.).

EXAMPLE 11

4,4'-Diamino-2-dimethylamino-carbonyl-methyloxy-diphenylsulfone

First, 2-ethoxycarbonylmethyloxy-4,4'-diaminodiphenylsulfone (3.4 g, 0.0097 mol) is dissolved in a mixture of aqueous 40% dimethylamine solution (68 ml) and tetrahydrofuran (100 ml). This solution is left to stand for 3 hours at ambient temperature, then evaporated to dryness in vacuo. The residue obtained is triturated with water (100 ml). The solid material is suction filtered and recrystallized from ethanol. The product thus obtained has a melting point of 238°–244° C. (decomp.).

EXAMPLE 12

4,4'-Diamino-2-methoxymethyl-diphenylsulfone (a) 2-Hydroxymethyl-4-nitro-chlorobenzene First, 2-carboxy-4-nitro-chlorobenzene (43.2 g, 0.215 mol) is dissolved in absolute tetrahydrofuran (500 ml), then triethylamine (30 ml, 0.215 mol) is added thereto. This mixture is cooled to −10° C. and, at this temperature, carbethoxy chloride (22 ml, 0.229 mol) is added dropwise thereto. The resulting mixture is stirred for a further hour at −10° to −5° C. The triethylamine hydrochloride formed is filtered off. The tetrahydrofuran solution is added dropwise over a period of 10 minutes at 0° C. to a solution of sodium borohydride (30 g, 0.789 mol) in water (100 ml). The reaction mixture is allowed to come back to ambient temperature with stirring within an hour. The reddish-orange solution obtained is mixed with 2N hydrochloric acid while cooling with ice and then extracted with ether. The ether extract is washed with water. After the ether has been evaporated off an oil remains which crystallizes after some time.

IR spectrum (methylene chloride):
3610 cm$^{-1}$ OH
1375 cm$^{-1}$ NO$_2$ (b) 2-Methoxymethyl-4-nitro-chlorobenzene The 2-hydroxymethyl-4-nitrochlorobenzene (18.7 g, 0.1 mol) is dissolved in absolute tetrahydrofuran (500 ml) and cooled to 0° C. The sodium alkoxide of the above compound is prepared with sodium hydride (4.8 g, 0.1 mol) (55% in oil). After 1 hour's reaction methyl iodide (14.2 g, 0.1 mol) is added dropwise with stirring at 0° C. The reaction mixture is kept at 0° C. for a further 3 hours with stirring. Then it is stirred without a cooling bath until ambient temperature is reached. The solvent is then evaporated off and the residue is taken up in ethyl acetate, the ethyl acetate phase is washed with water, dried and concentrated to dryness in vacuo. The remaining oil is crystallized from ethyl acetate.

| NMR (CDCL$_3$/CD$_3$OD): | 3.6 ppm | 3H Singlet |
|---|---|---|
| | 4.6 ppm | 2H Singlet |
| 80 MHz | 7.5–8.75 ppm | 3H Multiplet |

(c) 4'-Acetylamino-4-nitro-2-methoxymethyl-diphenylsulfone

Next 4-acetylanilido sulfinic acid (6.5 g, 0.0327 mol) is suspended in ethanol (50 ml) and sodium hydride (1.5 g, 0.033 mol) (55% in oil) is added in batches with stirring. The resulting sodium salt of the above acid is precipitated with ether and dried. Then, 4-acetylanilido sodium sulfinate (6.6 g, 0.03 mol) is refluxed with 2-methoxymethyl-4-nitro-chlorobenzene (6.1 g, 0.03 mol) in dimethylformamide (25 ml) for 5 hours. The reaction mixture is then poured onto ice water and extracted with ethyl acetate. The ethyl acetate extract is washed twice with water, dried over sodium sulfate and the ethyl acetate is evaporated off in vacuo. The solid residue is washed with isopropanol and petroleum ether.

| IR spectrum (CH$_2$Cl$_2$): | 3420 cm$^{-1}$ | NH |
|---|---|---|
| | 1710 cm$^{-1}$ | CO |
| | 1350 + 1530 cm$^{-1}$ | NO$_2$ |

(d) 4'-Acetylamino-4-amino-2-methoxymethyl-diphenylsulfone

Here, 4'-acetylamino-4-nitro-2-methoxymethyldiphenylsulfone (3.8 g, 0.0104 mol) is added in batches within 15 minutes to a boiling mixture of iron powder (3.4 g, 0.061 mol) in alcohol (25 ml), water (6 ml) and 36% hydrochloric acid (0.05 ml). The mixture is then refluxed for 2 hours. The reaction mixture is cooled, diluted with methanol, filtered over Celite and the methanol is evaporated. The residue is taken up in water and extracted with ethyl acetate. Then the ethyl acetate is evaporated off and an amorphous solid product is left.

| IR spectrum: (KBr): | 1680 cm$^{-1}$ | Amide I |
|---|---|---|
| | 1525 cm$^{-1}$ | Amide II |
| | 1140, 1320 cm$^{-1}$ | SO$_2$ |

(e) 4,4'-Diamino-2-methoxymethyl-diphenylsulfone

The 4'-acetylamino-4-amino-2-methoxymethyldiphenylsulfone (3.5 g, 0.01 mol) is heated to boiling in 3N hydrochloric acid for 15 minutes. The reaction solution is cooled, diluted with water and filtered. The aqueous filtrate is adjusted to pH 8–9 with dilute aqueous ammonia. The precipitate obtained is filtered off and washed with water.

| IR spectrum (KBr): | 1130 cm$^{-1}$ | SO$_2$ |
|---|---|---|
| | 1280 cm$^{-1}$ | SO$_2$ |

EXAMPLE 13

4,4'-Diamino-2-methylcarbonyl-diphenylsulfone

The title compound is prepared from 4'-acetamino-4-amino-2-methylcarbonyl-diphenylsulfone (prepared analogously to Example 12c and 12d) with hydrochloric acid analogously to Example 12e.

| IR spectrum (CH$_2$Cl$_2$): | 3485, 3390 cm$^{-1}$ | NH$_2$ |
|---|---|---|
| | 1695 cm$^{-1}$ | Ketone |
| | 1290, 1140 cm$^{-1}$ | SO$_2$ |

EXAMPLE 14

4,4'-Diamino-2-(1-hydroxyethyl)-diphenylsulfone

Here, 4,4'-diamino-2-methylcarbonyl-diphenylsulfone (1.6 g, 0.005 mol) (Example 13) suspended in 90% aqueous methanol (75 ml) is reduced with sodium borohydride (0.3 g, 0.0075 mol) at 20° C. After 30 minutes a clear solution is obtained. The methanol is evaporated off and the aqueous solution is diluted with more water. An oil is precipitated which is extracted with methylene chloride. After the solvent has been evaporated off a white amorphous product remains.

| NMR spectrum (CDCl$_3$): | 1.3 ppm | 2H Doublet |
|---|---|---|
| | 5.5 ppm | 1H Multiplet |
| 80 MHZ | 6.6–7.9 ppm | 7H Multiplet |

EXAMPLE 15

4,4'-Diamino-2-cyano-diphenylsulfone

Here, 4,4'-diamino-2-carbamoyl-diphenylsulfone (6.3 g, 0.021 mol) (prepared analogously to Example 18 is refluxed for 8 hours in thionyl chloride (45 ml). A yellowish-orange solution is obtained and the thionyl chloride is distilled off. A yellow foam remains which is suspended in water and made alkaline with ammonia solution. The base of the title compound thus obtained is suction filtered as an amorphous solid product and washed with water. The crude product is purified by chromatography on a silica gel column. (Eluant: 8 parts methylene chloride, 1 part methanol and 1 part acetone). The corresponding fractions are freed from the eluant and yield an amorphous, yellowish-white solid product.

Mass spectrum (CH$_5$): M+273 m/Z

EXAMPLE 16

4,4'-Diamino-2-aminomethyl-diphenylsulfone

Here, 4,4'-diamino-2-carbamoyl-diphenylsulfone (0.35 g, 0.0012 mol) is dissolved in absolute tetrahydrofuran (25 ml) and mixed with lithium aluminium hydride (0.15 g, 0.0036 mol). The mixture is stirred for 1 hour at 20° C. and then heated to 50° C. for 8 hours. The lithium aluminium hydride is decomposed with ice water and the reaction mixture is extracted with ether. After the solvent has been evaporated off, a solid yellow product is left behind, which is purified by chromatography over a silica gel column (eluant: 6 parts methylene chloride and 1 part methanol). After the eluant has been evaporated off from the corresponding fractions a yellowish amorphous product is left.

Mass spectrum (CH 5): M+277 m/z

EXAMPLE 17

4,4'-Diamino-2-hydroxymethyl-diphenylsulfone

Here, 4,4'-diamino-2-methoxycarbonyl-diphenylsulfone (0.23 g, 0.00075 mol) (J. Med. Chem. 14, 1168 (1971) is dissolved in absolute tetrahydrofuran (15 ml) and mixed with lithium aluminium hydride (0.07 g, 0.0019 mol). The mixture is stirred for 1 hour at 20° C. and then heated for 3 hours to 50° C. The excess lithium aluminum hydride is decomposed with water and then the reaction mixture is extracted with ether. After the solvent has been evaporated off, a yellowish-brown oil is left which is purified by chromatography over a silica gel column. (Eluant: 9 parts methylene chloride and 1 part methanol). The corresponding fractions yield a yellowish oil after evaporation of the eluant.

Mass spectrum (CH 5): M+278 m/z

EXAMPLE 18

4,4'-Diamino-2-(N-methylcarbamoyl)-diphenylsulfone

Here, 4,4'-diamino-2-chlorocarbonyl-diphenylsulfonedihydrochloride (0.95 g, 0.0025 mol) is suspended in methylene chloride (15 ml) and added to a solution of methylamine (0.31 g, 0.01 mol) in methylene chloride (20 ml). The mixture is stirred overnight at 20° C. Then the methylene chloride is evaporated off and the remaining solid residue is washed out with water. A white amorphous residue is left.

| IR spectrum (KBr): | 3480 + 3360 cm$^{-1}$ | NH$_2$ |
|---|---|---|
| | 1630 cm$^{-1}$ | Amide |
| | 1125 cm$^{-1}$ | SO$_2$ |

EXAMPLE 19

2-(N-Cyclohexyl-N-methyl-carbamoyl)-4,4'-diaminodiphenylsulfone

The title compound is prepared from 4,4'-diamino-2-chlorocarbonyl-diphenylsulfone-dihydrochloride and N-cyclohexyl-N-methylamine analogously to Example 18.

| IR spectrum (CH$_2$Cl$_2$): | 3490, 3400 cm$^{-1}$ | NH$_2$ |
|---|---|---|
| | 1620–1630 cm$^{-1}$ | Amide |
| | 1300, 1140 cm$^{-1}$ | SO$_2$ |

EXAMPLE 20

4,4'-Diamino-2-(N,N-dimethylamino)-diphenylsulfone (a) 2-Chloro-5-nitro-N,N-dimethyl-aniline Paraformaldehyde (63 g) is placed in 35% formic acid (1 liter) at 100° C., and 2-chloro-5-nitro-aniline (60 g) in 95% formic acid (560 ml) is added in batches. Then, the mixture is heated for 2 hours over a steam bath, the reaction mixture is evaporated, mixed with 2N NaOH (560 ml) and Na$_2$SO$_3$ (140 g), and extracted with methylene chloride. The organic phase is dried with magnesium sulfate, evaporated to dryness again and purified by chromatography over a column filled with silica gel. (Eluant: dichloromethane/cyclohexane=2:1). Yellow oil which is reacted further directly.

(b) 4'-Acetamino-2-(N,N-dimethylamino)-4-nitrodiphenylsulfone

The sodium salt of 4-acetylamino-phenylsulfinic acid (24 g), 2-chloro-5-nitro-(N,N-dimethyl)aniline (22 g) and absolute dimethylformamide (120 ml) are mixed together, refluxed for 28 hours, poured onto water, extracted with ethyl acetate and the organic phase is dried with magnesium sulfate and evaporated in vacuo. The residue is purified over a column filled with silica gel (eluant: dichloromethane/methanol=50:1). The fractions containing the desired product are evaporated and the residue is triturated with ether.

Yellow crystals. M.p.: 213°–216° C.

(c) 4'-Amino-2-(N,N-dimethylamino)-4-nitro-diphenylsulfone

Next, 4'-acetamino-2-(N,N-dimethylamino)-4-nitrodiphenylsulfone (10 g) is placed in semi conc. hydrochloric acid (50 ml) and heated for about 1 hour over a steam bath until a clear solution is obtained. Then it is cooled, made basic with 2N sodium hydroxide solution, extracted with dichloromethane, the organic phase is dried with magnesium sulfate and concentrated by evaporation. The residue is purified over a column filled with silica gel (eluant: dichloromethane/methanol=50:1).

Yellow crystals; m.p.: 164°–166° C.

(d) 4,4'-Diamino-2-(N,N-dimethylamino)-diphenylsulfone

The 4'-amino-2-(N,N-dimethylamino)-4-nitro-diphenylsulfone (6 g) is hydrogenated in methanol (200 ml) with Raney nickel (0.6 g) for 6 hours at ambient temperature under a pressure of 3 bar. Then the catalyst is removed by suction filtering, the filtrate is concentrated to dryness in vacuo and purified over a column filled with silica gel (eluant: dichloromethane/methanol=60:1).

Beige crystals; m.p. 196°–197° C.

EXAMPLE 21

4,4'-Diamino-2-(N-methyl-amino)diphenylsulfone

The title compound is prepared from 2-chloro-5-nitro-(N-methyl)-aniline and the sodium salt of 4-acetylaminophenylsulfinic acid analogously to Example 20. Hardened foam.

| IR spectrum (methylene chloride): | 3500, 3400 cm$^{-1}$ | NH$_2$ |
|---|---|---|
| | 1130, 1300 cm$^{-1}$ | SO$_2$ |

The 2-chloro-5-nitro-N-methyl-aniline was obtained as follows. First, 2-chloro-5-nitro-aniline (50 g), methyl iodide (82 g) and sodium carbonate (123.3 g) are refluxed for 16 hours in ethanol (1.2 liters). Then the insoluble precipitate is filtered off, the mother liquor is concentrated by evaporation and the residue is taken up in dichloromethane. The organic phase is washed with water, dried with magnesium sulfate and concentrated in vacuo. The residue is purified over a column filled with silica gel (eluant: dichloromethane/cyclohexane=1:2).

Orange crystals; m.p.: 106°–108° C.

EXAMPLE 22

4′-Amino-2,4-bis-(N,N-dimethyl-amino)-diphenylsulfone (a) 4′-Acetamino-4-amino-2-(N,N-dimethyl-amino) diphenylsulfone.

First, 4′-acetamino-2-(N,N-dimethyl-amino)-4-nitro-diphenylsulfone (4.5 g) is hydrogenated in methanol (200 ml) with Raney nickel (0.45 g) for two hours at ambient temperature under a pressure of 3 bar. Then the catalyst is filtered off, the filtrate is concentrated by evaporation and the residue is purified over a column filled with silica gel (eluant: dichloromethane/methanol=30:1).

Light brown crystals; m.p.: 117°–119° C.

(b) 4′-Acetamino-2,4-bis-(N,N-dimethyl-amino) diphenylsulfone

Paraformaldehyde (1.2 g) is dissolved in 95% formic acid (30 ml) with heating and 4′-acetamino-4-amino-2-(N,N-dimethyl-amino)-diphenylsulfone (2.3 g) is added. The reaction mixture is kept at 90° C. for 12 hours and then concentrated by evaporation in vacuo. A 2N sodium hydroxide solution (11 ml) and $Na_2SO_3$ (2.7 g) are then added. The mixture is extracted with ethylacetate, the extract is treated with active charcoal and magnesium sulphate, concentrated to dryness in vacuo and the residue is purified over a column filled with silica gel. (eluant: dichloromethane/methanol=30:1). Colorless oil which is immediately reacted further.

(c) 4′-Amino-2,4-bis-(N,N-dimethyl-amino)-diphenylsulfone

The 4′-acetamino-2,4-bis-(N,N-dimethyl-amino)-diphenylsulfone (1 g) is dissolved in 2N hydrochloric acid (50 ml) and heated for about 45 minutes over a steam bath. Then the mixture is cooled, made basic with 2N NaOH and extracted with methylene chloride. The organic phase is treated with active charcoal and magnesium sulphate, concentrated to dryness in vacuo and the residue is purified over a column filled with silica gel (eluant: dichloromethane/methanol=50:1). The residue of the desired fraction is triturated with ether.

Yellowish crystals; m.p.: 166°–168° C.

EXAMPLE 23

4′-Amino-4-(N-ethyl-amino)-2-trifluoromethyl-diphenylsulfone (a) 4′-Acetamino-4-nitro-2-trifluoromethyl-diphenylsulfone The sodium salt of 4-acetamino-phenylsulfinic acid (50 g) and 2-chloro-5-nitro-benzotrifluoride (48 g) in absolute dimethylformamide (260 ml) are refluxed for about 25 hours. The mixture is then cooled, poured onto water (2 liters) and extracted with dichloromethane. The organic phase is washed thoroughly with water, dried with magnesium sulphate and concentrated to dryness in vacuo. The residue is triturated with ether.

Light yellow crystals; m.p.: 228°–230° C.

(b) 4′-Acetamino-4-amino-2-trifluoromethyl-diphenylsulfone

The 4′-acetamino-4-nitro-2-trifluoromethyl-diphenylsulfone (30 g) is hydrogenated in methanol (800 ml) with Raney nickel (3 g) for 8 hours 40 minutes at ambient temperature under a pressure of 3 bar. Then the mixture is heated in order to bring the desired product into solution again. The catalyst is removed by suction filtering while still warm and the filtrate is concentrated in vacuo.

Beige crystals; m.p.: 220°–224° C.

(c) 4′-Acetamino-4-(N-ethyl-amino)-2-trifluoromethyl-diphenylsulfone

The 4′-acetamino-4-amino-2-trifluoromethyl-diphenylsulfone (3 g), acetaldehyde (6.7 g), molten sodium acetate (0.6 g) and Raney nickel (3 g) in ethanol (100 ml) are hydrogenated at 70° C. under a pressure of 5 bar for 11 hours. Then the catalyst is filtered off and the filtrate is concentrated to dryness in vacuo. The evaporation residue is purified by chromatography over a column filled with silica gel (eluant: dichloromethane/methanol=50:1).

Colorless crystals; m.p.: 157°–159° C.

(d) 4′-Amino-4-(N-ethyl-amino)-2-trifluoromethyl-diphenylsulfone

The 4′-acetamido-4-(N-ethyl-amino)-2-trifluoromethyl-diphenylsulfone (1.5 g) is stirred in semi-concentrated hydrochloric acid (20 ml) for about 5 minutes over a steam bath until a clear solution is obtained. Then it is poured onto water (50 ml), made basic with 2N sodium hydroxide solution and the precipitate obtained is suction filtered. This is taken up in dichloromethane. The solution is dried with magnesium sulphate, concentrated to dryness in vacuo and the residue is triturated with ether.

Yellowish crystals; m.p.: 133°–135° C.

EXAMPLE 24

4′-Amino-4-ethylamino-2-cyano-diphenylsulfone (a) 4′-Acetamino-4-amino-2-methoxycarbonyl-diphenylsulfone The title compound of this paragraph is prepared from 4′-acetamino-2-methoxycarbonyl-4-nitro-diphenylsulfate (Lit: J. Med. Chem. 1971, 1168) by catalytic hydrogenation analogously to Example 23b.

| Spectra: IR (KBr): | 3360, 3450 cm$^{-1}$ | $NH_2$ |
| --- | --- | --- |
|  | 1735 cm$^{-1}$ | ester-CO |
|  | 1650, 1680, 1550 cm$^{-1}$ | amide-CO |
| UV (methanol): | 257 nm and 240 nm. | |

(b) 4′-Acetamino-4-ethylamino-2-methoxycarbonyl-diphenylsulfone

The title compound of this paragraph is prepared from 4′-acetamino-4-amino-2-methoxycarbonyl-diphenylsulfone, acetaldehyde and catalytically activated hydrogen analogously to Example 23c.

Amorphous product.

| Spectra: IR (CH$_2$Cl$_2$): | 3440 cm$^{-1}$ | —NH |
| --- | --- | --- |
|  | 1740 cm$^{-1}$ | ester-CO |
|  | 1710, 1520 cm$^{-1}$ | amide-CO |
| UV (methanol): | 260 nm, 300 nm. | |

(c) 4-Ethylamino-4′-amino-2-methoxycarbonyl-diphenylsulfone

The title compound of this paragraph is prepared from 4′-acetamino-4-ethylamino-2-methoxycarbonyl-diphenylsulfone and hydrochloric acid analogously to Example 23d.

M.p.: 155°–156° C.

(d) 4-Ethylamino-4′-amino-2-carboxy-diphenylsulfone

The 4-ethylamino-4'-amino-2-methoxycarbonyl-diphenylsulfone (39 g, 0.116 mol) is refluxed for 4 hours with sodium hydroxide (10 g) in a mixture of water (70 ml) and methanol (350 ml). After cooling, the mixture is suction filtered to remove a small quantity of an insoluble material. The filtrate is adjusted to pH 4 with hydrochloric acid whereupon the reaction product is precipitated in the form of crystals. These are suction filtered, washed with ice water and dried.

M.p.: 116°–122° C. (decomp.).

(e) 4-Ethylamino-4'-amino-2-cyano-diphenylsulfone

The 4-ethylamino-4'amino-2-carboxy-diphenylsulfone (37 g, 0.115 mol) is refluxed for 45 minutes in thionyl chloride (370 ml). The mixture is concentrated to dryness in vacuo and the residue is carefully mixed with cold concentrated aqueous ammonia. From this 4-ethylamino-4'-amino-2-carbamoyl-diphenylsulfone is obtained, which is suction filtered, washed with water, dried and dehydrated without any further purification with thionyl chloride to give the nitrile. The above amide (32 g, about 0.1 mol) in thionyl chloride (220 ml) is refluxed for 2.75 hours. The reaction mixture is evaporated in vacuo and the crude product is purified by repeated chromatography on silica gel (eluant: methylene chloride/methanol=40:1).

M.p.: 177°–183° C.

EXAMPLE 25

4'-Amino-2-methyl-4-n-propylamino-diphenylsulfone (a) 2-Methyl-4'-nitro-4-(N-n-propyl-N-tosyl-amino)-diphenylsulfone First, 2-methyl-4'-nitro-4-tosylamino-diphenylsulfone (2.5 g), n-propyl iodide (0.8 ml) and anhydrous potassium carbonate (0.9 g) are heated to 60° C. for 17 hours in dimethylformamide (30 ml) with stirring. After cooling, the mixture is poured onto water. The solids precipitated are taken up in methylene chloride. The methylene chloride phase is separated, washed with water, dried over sodium sulphate and concentrated to dryness. When the residue is recrystallized from petroleum ether/ethyl acetate, yellow crystals are obtained:

M.p.: 132°–135° C.

(b) 2-Methyl-4'-nitro-4-n-propylamino-diphenylsulfone

A solution of the 2-methyl-4'-nitro-4-(N-n-propyl-N-tosyl-amino)-diphenylsulfone (2.48 g) is left to stand for 4 hours at ambient temperature in concentrated sulfuric acid (25 ml). Then, it is poured into ice/concentrated ammonium hydroxide solution and the solids precipitated are extracted with methylene chloride. The methylene chloride phase is washed with water, dried over sodium sulphate and concentrated to dryness in vacuo and in this way the desired compound is obtaihed in the form of a yellow solid.

(c) 4'-Amino-2-methyl-4-n-propylamino-diphenylsulfone

The 2-methyl-4'-nitro-4-n-propylamino-diphenylsulfone (1.6 g) is dissolved in methanol (60 ml) and hydrogenated at ambient temperature in the presence of 10% palladium/charcoal (0.5 g) under a hydrogen pressure of 50 psi. After the uptake of hydrogen has ended (15 minutes) the catalyst is filtered off and the methanolic solution is concentrated (to 10 ml). The colorless crystals precipitated, m.p. 170°–173° C., are suction filtered.

EXAMPLE 26

4'-Amino-4-cyclohexylamino-2-methyl-diphenylsulfone (a) 4-cyclohexylamino-2-methyl-4'-nitro-diphenylsulfone First, 4-amino-2-methyl-4'-nitro-diphenylsulfone is dissolved in methylene chloride (120 ml). Molecular sieve A4 (15 g) and ethereal hydrochloric acid (2 ml) are added to this solution and then cyclohexanone (2 ml) and sodium cyanoborohydride (1 g) are added with stirring. The mixture is left to stand overnight at ambient temperature and filtered. The filtrate is stirred with 2N hydrochloric acid (50 ml) and then with 2N ammonia (200 ml) for 10 minutes. The methylene chloride phase is removed, washed with water, dried over sodium sulphate and concentrated. The solid yellow residue is chromatographed on silica gel using methylene chloride as eluant. The eluants containing the substance are evaporated and when the residue is recrystallized from ether/petroleum ether, yellow crystals are obtained, m.p. 116°–119° C.

(b) 4'-Amino-4-cyclohexylamino-2-methyl-diphenylsulfone

The title compound of this paragraph is prepared from 4-cyclohexylamino-2-methyl-4'-nitro-diphenylsulfone with hydrogen and palladium/charcoal analogoulsy to Example 25c.

M.p.: 180°–183° C.

EXAMPLE 27

4'-Amino-2-methyl-4-n-propylamino-diphenylsulfone

Here, 2-methyl-4'-nitro-4-propylidenamino-diphenylsulfone (1.5 g) (prepared from 4-amino-2-methyl-4'-nitro-diphenylsulfone, propionaldehyde, titanium(IV) chloride and potassium carbonate in dichloromethane) is dissolved in methanol (50 ml) and hydrogenated in the presence of palladium/charcoal (0.5 g) at ambient temperature under a hydrogen pressure of 50 psi until the uptake of hydrogen has ended. After the catalyst is removed, the remaining mother liquor is concentrated to dryness in vacuo. The residue is chromatographed over silica gel with methylene chloride as the eluant. When the eluants containing the substance are evaporated, colorless crystals are obtained, m.p.: 170°–173° C.

EXAMPLE 28

4'-Amino-2-methyl-4-methylamino-diphenylsulfone

The title compound is prepared from 2-methyl-4-methylamino-4'-nitro-diphenylsulfone with hydrogen and palladium/charcoal analogously to Example 25c.

M.p.: 150°–153° C.

EXAMPLE 29

4-Ethylamino-4'-amino-2-methyl-diphenylsulfone

The title compound is prepared from 4-ethylamino-2-methyl-4'-nitro-diphenylsulfone with hydrogen and palladium/charcoal analogously to Example 25c.

M.p.: 166°–167° C.

EXAMPLE 30

4'Amino-4-isopropylamino-2-methyl-diphenylsulfone

The title compound is prepared from 4-isopropylamino-2-methyl-4'-nitro-diphenylsulfone with hydrogen and palladium/charcoal analogously to Example 25c.
M.p.: 149°–150° C.

EXAMPLE 31

4'-Amino-4-n-hexylamino-2-methyl-diphenylsulfone

The title compound is prepared from 4-n-hexylamino-2-methyl-4'-nitro-diphenylsulfone with hydrogen and palladium/charcoal analogously to Example 25c.
M.p.: 116°–118° C.

EXAMPLE 32

4'-Amino-4-cyclopentylamino-2-methyl-diphenylsulfone

The title compound is prepared from 4-cyclopentylamino-2-methyl-4'-nitro-diphenylsulfone with hydrogen and palladium/characoal analogously to Example 25c.
M.p.: 176°–178° C.

EXAMPLE 33

4'-Amino-4-dimethylamino-2-methyl-diphenylsulfone

The title compound is prepared from 4-dimethylamino-2-methyl-4'-nitro-diphenylsulfone with hydrogen and palladium/charcoal analogously to Example 25c.
M.p.: 221°–223° C.

EXAMPLE 34

4'-Amino-4-n-hexylamino-2-methyl-diphenylsulfone

The title compound is prepared from 4'-acetamino-4-(N-n-hexyl-N-tosyl-amino)-2-methyl-diphenylsulfone with phenol and hydrobromic acid analogously to Example 6.
M.p.: 116°–118° C.

EXAMPLE 35

4'-Amino-4-isopropylamino-2-methyl-diphenylsulfone

The title compound is prepared from 4'-acetamino-4-(N-isopropyl-tosyl-amino)-2-methyl-diphenylsulfone with phenol and hydrobromic acid analogously to Example 6.
M.p.: 149°–150° C.

EXAMPLE 36

4'-Amino-2-chloro-4-cyclohexylamino-diphenylsulfone

The title compound is prepared from 4'-acetamino-2-chloro-4-cyclohexyl-amino-diphenylsulfone and 3N hydrochloric acid analogously to Example 22c.
M.p.: 197°–199° C.

EXAMPLE 37

By hydrolysis of a corresponding compound of formula IIIa

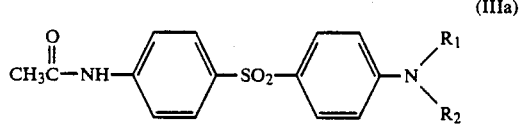

(IIIa)

The following compounds are obtained analogously to Example 22c:

| $-N\begin{matrix}R_1\\R_2\end{matrix}$ | melting point |
|---|---|
| NHCH$_3$ | 150–153° |
| NHC$_2$H$_5$ | 166–167° |
| NHC$_3$H$_7$ | 170–173° |
| NH-isoC$_3$H$_7$ | 149–150° |
| NH—C$_6$H$_{13}$ | 116–118° |
| NH-Cyclopentyl | 176–178° |
| NH-Cyclohexyl | 180–183° |
| N(CH$_3$)$_2$ | 221–223° |

EXAMPLE 38

4-Ethylamino-4'-amino-2-hydroxymethyl-diphenylsulfone

The title compound is prepared from 4-ethylamino-4'-amino-2-methoxycarbonyl-diphenylsulfone and lithium aluminium hydride analogously to Example 17.
M.p.: 148°–151°

EXAMPLE 39

4'Amino-2-methylamino-4-n-propylamino-diphenylsulfone

The title compound is prepared from 4'-acetamino-2-methylamino-4-n-propylamino-diphenylsulfone and 20% hydrochloric acid analogously to Example 22c.
M.p.: 142°–143° C.

EXAMPLE I

Tablets containing 4,4'-diamino-2-cyano-diphenylsulfone

| Composition: | |
|---|---|
| 1 Tablet contains: | |
| Active substance | 100.0 mg |
| Corn starch, suitable for making directly into tablets | 60.0 mg |
| Lactose, suitable for making directly into tablets | 38.0 mg |
| Magnesium stearate | 2.0 mg |
| | 200.0 mg |

Preparation:
The substances are evenly mixed and compressed to form tablets.

EXAMPLE II

Tablets containing 4,4'-diamino-2-cyano-diphenylsulfone

| 1 Tablet contains: | |
|---|---|
| Active substance | 200.0 mg |
| Corn starch, suitable for making directly into tablets | 120.0 mg |
| Lactose, suitable for making directly into tablets | 76.0 mg |
| Magnesium stearate | 4.0 mg |
| | 400.0 mg |

Preparation:
As in Example I.

EXAMPLE III

Coated tablets containing 4,4'-diamino-2-cyano-diphenylsulfone and pyrimethamine

| 1 Tablet core contains: | |
| --- | --- |
| Active substance | 50.0 mg |
| Pyrimethamine | 6.25 mg |
| Corn starch, suitable for making directly into tablets | 40.0 mg |
| Lactose, suitable or making directly into tablets | 22.75 mg |
| Magnesium stearate | 1.0 mg |
| | 120.0 mg |

Preparation:
As in Example I.
Coating:
The cores are coated by known methods with a coating of sugar and talc (30 mg total).

EXAMPLE IV

Tablets containing 4,4'-diamino-2-cyano-diphenylsulfone and pyrimethamine

| 1 Tablet contains: | |
| --- | --- |
| Active substance | 100.0 mg |
| Pyrimethamine | 12.5 mg |
| Corn starch, suitable for making directly into tablets | 60.0 mg |
| Lactose, suitable for making directly into tablets | 25.5 mg |
| Magnesium stearate | 2.0 mg |
| | 200.0 mg |

Preparation:
As in Example I.

EXAMPLE V

Ampoules containing 4,4'-diamino-2-cyano-diphenylsulfone (i.m. and s.c. crystal suspension)

| 1 Ampoule contains: | |
| --- | --- |
| Active substance | 100.0 mg |
| Sodium chloride | 15.0 mg |
| Doubly distilled water ad. | 3.0 ml |

Preparation:
The active substance is finely ground (particle size <5 μm). The substance is homogenously distributed in the sodium chloride solution. The suspension is transferred into ampoules (3 ml) and sterilized for 20 minutes at 121° C.

EXAMPLE VI

Ampoules containing 4,4'-diamino-2-cyano-diphenylsulfone (i.m. and s.c. crystal suspension) and pyrimethamine (combination with pyrimethamine)

| 1 Ampoule contains: | |
| --- | --- |
| Active substance | 100.0 mg |
| Pyrimethamine | 12.5 mg |
| Sodium chloride | 15.0 mg |
| Doubly distilled water ad. | 3.0 ml |

Preparation:
The active substances are finely ground (particle size <5μ). The substances are homogeneously distributed in the sodium chloride solution. The suspension is transferred into ampules (3 ml) and sterilized for 20 minutes at 121° C.

What is claimed is:

1. A pharmaceutical composition of matter for treating a bacterial infection in a warm-blooded animal which comprises a therapeutically effective amount of a compound of formula

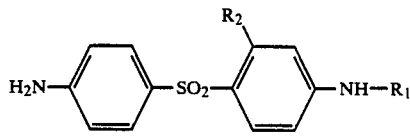

wherein $R_1$ is hydrogen or $C_1$–$C_3$ alkyl and $R_2$ is hydroxy, $C_1$–$C_3$ alkyl, $C_1$–$C_3$ alkylcarbonyl or cyano, or a non-toxic, pharmaceutically acceptable salt thereof, a therapeutically effective amount of pyrimethamine or trimethoprin, and a non-toxic pharmaceutically acceptable carrier.

2. The composition of claim 1 which comprises 4,4'-diamino-2-methyl-4-n-propylamino-diphenylsulfone or a non-toxic, pharmaceutically acceptable salt thereof.

* * * * *